(12) United States Patent
Lee

(10) Patent No.: US 9,801,534 B2
(45) Date of Patent: Oct. 31, 2017

(54) TELESCOPIC INTUBATION TUBE WITH DISTAL CAMERA

(71) Applicant: Jonathan Y. Lee, San Diego, CA (US)

(72) Inventor: Jonathan Y. Lee, San Diego, CA (US)

( * ) Notice: Subject to any disclaimer, the term of this patent is extended or adjusted under 35 U.S.C. 154(b) by 735 days.

(21) Appl. No.: 13/840,352

(22) Filed: Mar. 15, 2013

(65) Prior Publication Data

US 2014/0018615 A1    Jan. 16, 2014

Related U.S. Application Data

(63) Continuation-in-part of application No. 13/549,218, filed on Jul. 13, 2012, now abandoned.

(51) Int. Cl.
| | | |
|---|---|---|
| *A61B 1/00* | (2006.01) | |
| *A61B 1/04* | (2006.01) | |
| *A61B 1/06* | (2006.01) | |
| *A61B 1/267* | (2006.01) | |
| *A61M 16/04* | (2006.01) | |

(Continued)

(52) U.S. Cl.
CPC ............ *A61B 1/267* (2013.01); *A61B 1/0051* (2013.01); *A61B 1/00165* (2013.01); *A61B 1/00195* (2013.01); *A61B 1/05* (2013.01); *A61B 1/0676* (2013.01); *A61B 1/2673* (2013.01);
(Continued)

(58) Field of Classification Search
CPC .............. A61B 1/00071; A61B 1/0008; A61B 1/00089; A61B 1/00188; A61B 1/0019; A61B 1/00195; A61B 1/005; A61B 1/0051; A61B 1/0052; A61B 1/0053; A61B 1/0055; A61B 1/0057; A61B 1/0058; A61B 1/01; A61B 1/05; A61B 1/051; A61B 1/233; A61B 1/24; A61B 1/267; A61B 1/2673; A61B 1/2676
USPC ................ 600/104, 106, 107, 113, 120–125, 600/185–199; 128/200.26, 207.14
See application file for complete search history.

(56) References Cited

U.S. PATENT DOCUMENTS

| | | |
|---|---|---|
| 4,150,676 A | 4/1979 | Jackson |
| 4,622,965 A | 11/1986 | Teeple |

(Continued)

FOREIGN PATENT DOCUMENTS

WO    20100655566 A2    6/2010

OTHER PUBLICATIONS

International Search Report and Written Opinion for corresponding application No. PCT/US2013/049548, mailed on Oct. 18, 2013 in 9 pages.

*Primary Examiner* — Ryan Henderson
(74) *Attorney, Agent, or Firm* — Gorman IP Law, APC

(57) ABSTRACT

An extendable intubation device is disclosed that includes a tube assembly having a plurality of elongated tubes. Within the assembly, a base tube is coupled with an extension tube to maintain a continuous fluid pathway along the tube assembly during a fore-and-aft movement of the extension tube relative to the base tube. The extendable intubation device can include a camera system to allow a user (e.g. physician) to visually monitor the advancement of the distal end of the extension tube into the trachea of the patient. The camera system can include a sensor portion attached to the distal end of the extension tube and a monitor portion. A conductive wire connects the sensor portion to the monitor portion. The monitor portion of the camera system can be provided as an eyepiece at the proximal end of the intubation device and/or as a stand alone display.

11 Claims, 4 Drawing Sheets

(51) Int. Cl.
    *A61B 1/005*     (2006.01)
    *A61B 1/05*     (2006.01)

(52) U.S. Cl.
    CPC ....... *A61B 1/2676* (2013.01); *A61M 16/0488* (2013.01); *A61M 2205/502* (2013.01)

(56) References Cited

U.S. PATENT DOCUMENTS

| | | | |
|---|---|---|---|
| 5,263,472 A | | 11/1993 | Ough |
| 5,733,242 A | * | 3/1998 | Rayburn et al. .............. 600/120 |
| 5,800,342 A | | 9/1998 | Lee et al. |
| 2002/0072652 A1 | | 6/2002 | Berci et al. |
| 2005/0272975 A1 | * | 12/2005 | McWeeney et al. ......... 600/113 |
| 2008/0308098 A1 | | 12/2008 | Schwartz et al. |
| 2010/0099949 A1 | * | 4/2010 | Tilson et al. ................. 600/116 |
| 2010/0292535 A1 | * | 11/2010 | Paskar .......................... 600/113 |
| 2012/0022326 A1 | * | 1/2012 | Jaime ............... A61M 25/0147 600/109 |
| 2012/0298112 A1 | | 11/2012 | Paskar |

\* cited by examiner

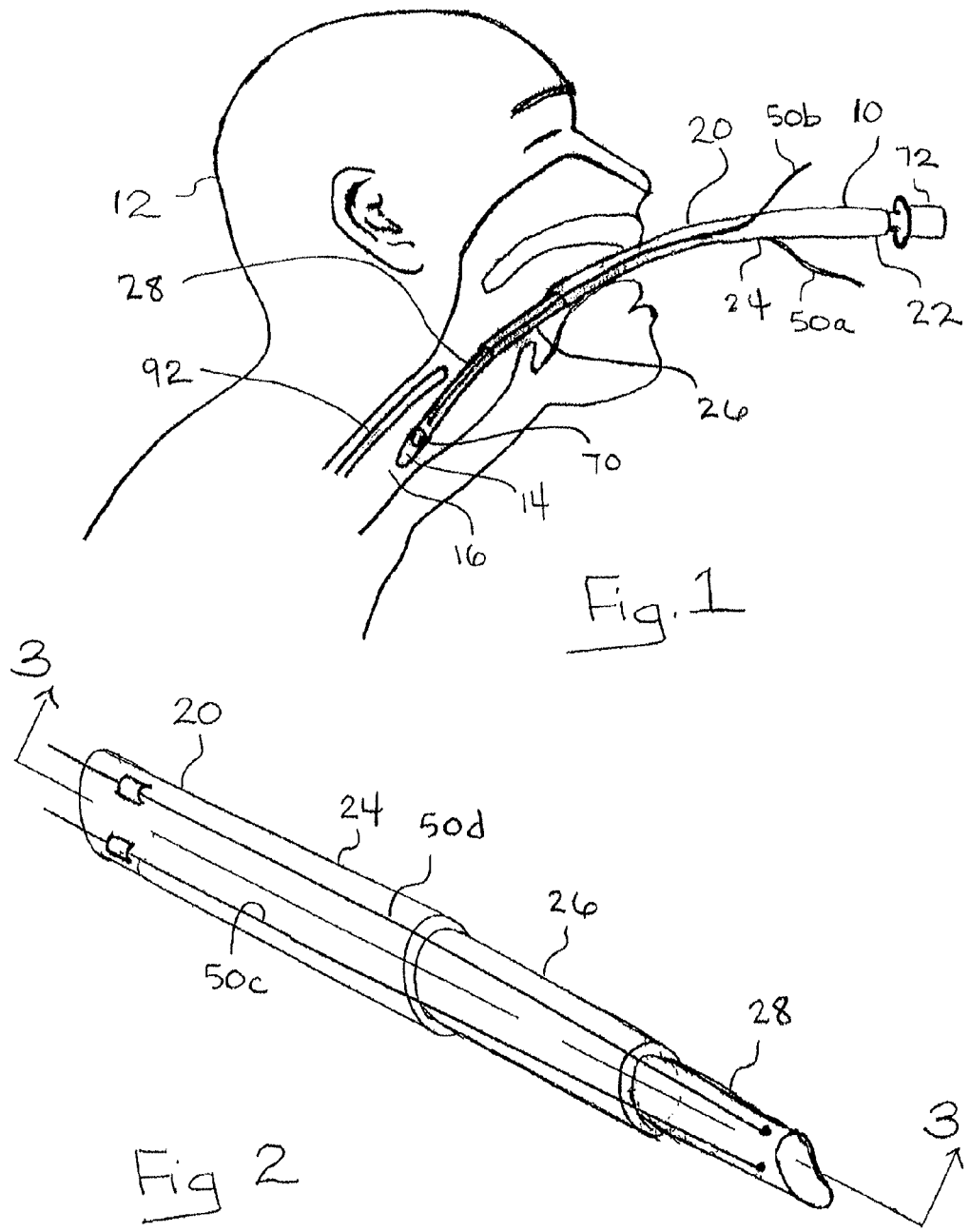

TELESCOPIC INTUBATION TUBE WITH DISTAL CAMERA

This application is a continuation-in-part of application Ser. No. 13/549,218, filed Jul. 13, 2012, which is currently pending. The contents of application Ser. No. 13/549,218 are incorporated herein by reference.

FIELD OF THE INVENTION

The present invention pertains generally to medical devices. More particularly, the present invention pertains to tracheal intubation tubes. The present invention is particularly, but not exclusively, useful as an extendable and steerable intubation tube assembly that can be guided within the respiratory tract and into a patient's trachea.

BACKGROUND OF THE INVENTION

Intubation is a medical procedure that is used to establish and maintain the patency of a patient's airway. In nearly all cases, the procedure is performed by inserting the distal end of an intubation tube into the patient's upper respiratory tract and then carefully advancing the tube through the larynx and into the patient's trachea. Although tracheal intubation is typically performed through the mouth (orotracheal intubation), it can also be performed through the nose (nasotracheal intubation).

Tracheal intubation is often employed in emergency rooms under circumstances which require a physician to intubate a difficult patient quickly and without complication. This is no easy task. For one, it is generally desirable to use a large diameter tube to provide as much airflow as possible. This requirement for a relatively large tube can compound the difficulties associated with trying to guide the intubation tube through the twists and turns within the respiratory tract necessary to reach the trachea.

As indicated above, during an intubation procedure, a relatively large diameter tube must be passed through the somewhat fragile larynx and into the trachea. This procedure must be performed delicately as undesirable complications can result if the airway is scraped or scratched. Generally, during advancement of the intubation tube, certain anatomical features must be identified to establish a correct pathway into the trachea and avoid entry into the esophagus. In fact, one of the biggest complications associated with these procedures is the failure to properly intubate the patient. Once the correct path is identified, it is not always easy to coax a flexible tube onto a desired pathway leading into the trachea.

In addition to the concerns cited above, substantial differences in the length and shape of the path that must be navigated by the intubation tube exist across the general patient population due to differences in patient height, weight, oral anatomy and age. In this regard, there is rarely time in the emergency room setting to identify and find a preformed intubation tube having a shape and size that perfectly matches a patient.

In light of the above, it is an object of the present invention to provide an extendable intubation tube that can be controllably guided through the respiratory system and into the trachea. Another object of the present invention is to provide an intubation device having a system to visually assist the user in guiding the device into the trachea. Still another object of the present invention is to provide an extendable intubation tube that can fit a relatively large portion of the general patient population and provide an optimal airway for all patients. Yet another object of the present invention is to provide a Telescopic Intubation Tube with Distal Camera and corresponding methods of use which are easy to use, relatively simple to implement, and comparatively cost effective.

SUMMARY OF THE INVENTION

In accordance with the present invention, an extendable intubation device includes a tube assembly having a plurality of elongated tubes. For the intubation device, each tube has a proximal end, a distal end and is formed with a lumen extending between the tube's distal and proximal ends. Within the assembly, a first tube (base tube) is coupled with an adjacent second tube (extension tube) to maintain a continuous fluid pathway along the tube assembly during a fore-and-aft movement of the extension tube relative to the base tube. For example, in one embodiment, the proximal end of the extension tube can be co-axially mounted within the lumen of the base tube at the base tube's distal end. On the other hand, when base tubes having relatively small lumens are used (for example, for infants), the extension tube(s) may be mounted, e.g. clipped on, the external surface of the base tube. When an additional tube (e.g. a second extension tube) is included in the assembly, the second extension tube can be coupled with the first extension tube to maintain a continuous fluid pathway along the tube assembly during a fore-and-aft movement of the second extension tube relative to the first extension tube.

With the tubes assembled, the length of the extendable intubation device can be manually adjusted by a control unit. In more structural detail, the control unit can include at least one control wire(s). The control wire (or each wire when more than one is used) has an end that is attached to the distal end of the most distal extension tube. For the control unit, the wire(s) are sized to be long enough to ensure that the proximal end of each wire remains at an extracorporeal location throughout the intubation procedure. With this arrangement, the control unit can be employed to reciprocally move one or more of the extension tubes in a fore-and-aft movement relative to the base tube.

For the intubation device, one, some or all of the tubes in the tube assembly can be of a flexible construction such that the flexible tube(s) can bend under the influence of the control unit. With this structure, one or more of the control wire(s) can be manipulated to bend the distal end of the tube assembly and steer the intubation device into a patient's trachea. For example, a three wire or a four wire configuration may be used. For these configurations, the attachment points for the wires at the distal end of the tube assembly are typically uniformly spaced around the distal tube.

Also for the present invention, structures can be formed in the tubes to limit, and in some cases prevent, a relative rotation between adjacent tubes in the tube assembly. These structures, or additional structures, can also be used to limit the distal travel of one tube relative to another (i.e. an adjacent, more proximal tube).

The intubation device can also include an optical assembly to allow a user (e.g. physician) to visually monitor the advancement of the distal end of the tube assembly into the trachea of the patient. For this purpose, the optical assembly can include an optical fiber that extends through the tube assembly. For the optical assembly, the optical fiber has an end that is attached to the distal end of the most distal extension tube. The other end (i.e. the proximal end) of the fiber can be attached to an eyepiece, which remains at an extracorporeal location throughout the intubation procedure.

In some implementations, a light source can be provided to introduce light into the optical fiber and illuminate the anatomical portions of the body near the distal end of the tube assembly.

In another embodiment of an intubation device, the optical assembly can include a camera system to allow a user (e.g. physician) to visually monitor the advancement of the distal end of the tube assembly into the trachea of the patient. For this embodiment, the camera system can include a sensor portion, a monitor portion and one or more conductive wire(s). For the camera system, the sensor portion is attached to the distal end of the most distal extension tube. The monitor portion of the camera system can be provided as an eyepiece at the proximal end of the intubation device and/or as a stand-alone display. The conductive wire is operably connected to the sensor portion and extends through the tube assembly to the monitor portion. In some implementations, a light source can be provided at the distal end of the distal most tube to illuminate the anatomical portions of the body near the distal end of the tube assembly.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a patient with portions removed to expose the patients upper respiratory tract; shown intubated with an extendable intubation device in accordance with the present invention;

FIG. 2 is a perspective view of a tube assembly and control unit for use in the extendable intubation device shown in FIG. 1;

DESCRIPTION OF THE PREFERRED EMBODIMENTS

Figures 3, 4, 5, 6:
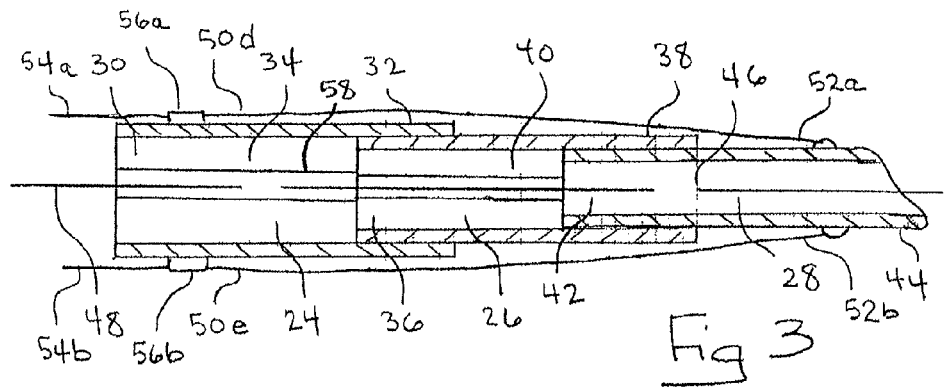
FIG. 3 is a cross sectional view of the tube assembly shown in FIG. 2 as seen along line 3-3 in FIG. 2.
FIG. 4 is a perspective view of a tube with portions removed to reveal the inner tube wall which includes a keyway formed thereon.
FIG. 5 is a perspective view of a tube showing a key extending from the outer tube surface for cooperation with the keyway shown in FIG. 4.
FIG. 6 is a schematic view of an optical assembly having a light, eyepiece and optical fiber.

Referring initially to FIG. 1, an extendable intubation device 10 is shown positioned within a patient 12 after an orotracheal intubation of the patient 12. As shown, the distal end 14 of the device 10 has been positioned in the trachea 16 of the patient. FIG. 1 further shows that the device 10 includes a tube assembly 20 that extends from the distal end 14 of the device 10 to a proximal end 22 of the device which remains at an extracorporeal location throughout the intubation procedure.

FIGS. 2 and 3 show the tube assembly 20 in greater detail. As shown there, the tube assembly can include an elongated base tube 24 and elongated extension tubes 26, 28. Although the device 10 that is shown in FIGS. 1-3 is illustrated as having three tubes, it is to be appreciated that more than three tubes and as few as two tubes (i.e. a base tube and one extension tube) may be used for the extendable intubation device described herein.

FIGS. 2 and 3 further show that the base tube 24 has a proximal end 30, a distal end 32 and is formed with a lumen 34 extending between the distal end 32 and proximal end 30. Similarly, extension tube 26 has a proximal end 36, a distal end 38 and is formed with a lumen 40 extending between the distal end 38 and proximal end 36 and extension tube 28 has a proximal end 42, a distal end 44 and is formed with a lumen 46 extending between the distal end 44 and proximal end 42.

Continuing with reference to FIGS. 2 and 3, it can be seen that the tubes 24, 26, 28 in the tube assembly 20 are telescopically arranged. Specifically, as shown, tubes 24, 26, 28 are each cylindrically shaped and are each centered on common axis 48 with the proximal end 42 of the extension tube 28 co-axially mounted within the lumen 40 of extension tube 26 at the distal end 38 of extension tube 26. Similarly, the proximal end 36 of the extension tube 26 is co-axially mounted within the lumen 34 of base tube 24 at the distal end 32 of base tube 24.

FIGS. 1-3 also show that the distal most tube (i.e. tube 28) is typically formed with a beveled tip making it easier to pass through the vocal cords. Each tube in the tube assembly 20 can be made of the same material and wall thickness, or, the tube thickness and tube material may vary among the tubes. For example, one or more of the extension tubes 26, 28 may be more flexible than the base tube 24, either by material selection, wall thickness or both. In one arrangement, the base tube 24 is made to be rigid enough to allow the user to insert the tube through the mouth/nose and into the larynx while the extension tube(s) are flexible. For some implementations, the length of each extension tube 26, 28 may be in the range of about 3-5 cm. Generally, the base tube 24 may be longer than the extension tubes 26, 28, as shown in FIG. 1. Tube materials can include but are not necessarily limited to polyvinyl chloride, silicone rubber, latex rubber or a metal such as stainless steel. In some cases, one or more of the tubes may be armored to give it strength and flexibility, for example, a spiral of wire may be embedded into the wall of the tube. For some applications, the tube assembly 20 can include a standard cuff, such as a balloon (not shown) affixed to the distal extension tube 28.

FIGS. 1-3 show that the overall length of the tube assembly 20 can be manually adjusted by a control unit having one or more control wires 50a-e. Although embodiments are shown having two wires (FIG. 1) and four wires (FIGS. 2 and 3), it to be appreciated that more than four and as few as one control wire may be used in the extendable intubation devices disclosed herein. For the embodiments shown, the control wires 50a-e can be relatively stiff and made of a metal such as stainless steel.

As best seen in FIG. 3, each control wire 50d,e has a respective end 52a,b that is attached to the distal end 44 of the most distal extension tube 28. Typically, as shown, the attachment points for the wires 50d,e at the distal end 44 of the tube 28 are uniformly spaced around the extension tube 28.

Additionally, a wire (not shown) may be attached to the distal end 38 of the intermediate extension tube 26. For the present invention, the technique used to affix the control wire 50d,e to the extension tube 28 can be any technique known in the pertinent art for attaching a control wire to a plastic or metal tube such as adhesive bonding, brazing or a mechanical attachment. It can also be seen that the wires 50d,e are sized to be long enough to ensure that the proximal end 54a,b of each wire 50d,e remains at an extracorporeal location throughout the intubation procedure. These proximal ends 54a,b can be left free for manipulation by the user.

Although the control wires 50d,e are shown positioned externally to the tube assembly 20, it is to be appreciated that portions (or all) of each wire may be located within the tube assembly 20 (i.e. the wires 50d,e may pass through in the lumens 34, 40, 46 of the tubes 24, 26, 28). For example, this may allow the extension tube(s) and wires to be extubated while leaving the base tube 24 positioned in the patient. Moreover, as shown, wire guides 56a,b may be employed to constrain lateral wire movement. Although one guide 56a,b is shown for each wire 50d,e, it is to be appreciated that more than one guide 56a,b per wire 50d,e may be employed and that guides 56a,b may be employed on extension tubes 26, 28, or internally when the wires 50d,e are passed within the tube assembly 20.

With the arrangement described above, the control wires 50d,e can be employed to reciprocally move one or more of the extension tubes 26, 28 in a fore-and-aft movement relative to the base tube 24. As indicated above, one, some or all of the tubes 24, 26, 28 in the tube assembly 20 can be of a flexible construction such that the flexible tube(s) can bend under the influence of the control wires 50d,e. With reference to FIG. 1, it can be seen one or more of the control wires 50a,b, can be manipulated to bend the distal end 14 of the device 10 and steer the distal end 14 into the patient's trachea 16.

Referring now to FIGS. 3-5, it can be seen that structures can be provided to limit, and in some cases prevent, a relative rotation between adjacent tubes 24, 26, 28 in the tube assembly 20 and/or limit the distal travel of an extension tube 26, 28. In greater detail, FIG. 4 shows a base tube 24 having a keyway 58 formed on the inner wall 60 of the base tube 24. As shown, the keyway 58 may extend from the proximal end 30 of the extension tube 26 to an end 62 located at a distance from the distal edge 64 of the base tube 24. Also, FIG. 5 shows an extension tube 26 having a key 66, complementary to the keyway 58 shown in FIG. 4, formed on the outer wall 68 of the extension tube 26, for example, near the proximal end 36 of extension tube 26. In use, the key 66 may be slid into the keyway 58 when the tubes 24, 26 are assembled together. The size and positions/length of the key 66 and keyway 58 may be designed to selectively limit relative rotation and/or distal travel of the extension tube 26 relative to the base tube 24. A similar key/keyway system may be used to limit relative rotation and/or distal travel of the extension tube 28 relative to the extension tube 26.

Cross referencing FIGS. 1 and 6, it can be seen that the intubation device 10 can also include an optical assembly 69 to allow a user (e.g. physician) to visually monitor the advancement of the distal end 14 of the device 10 into the trachea 16 of the patient 12. As shown, the optical assembly 69 can include an optical fiber 70 that extends through the tube assembly 20 from the distal end 14 to an eyepiece 72 which remains at an extracorporeal location throughout the intubation procedure. FIG. 6 shows that a light source 74 can be spliced together with the eyepiece 72 to introduce light into the optical fiber 70 and illuminate the anatomical portions of the body near the distal end 14 of the device 10.

Figure 7:
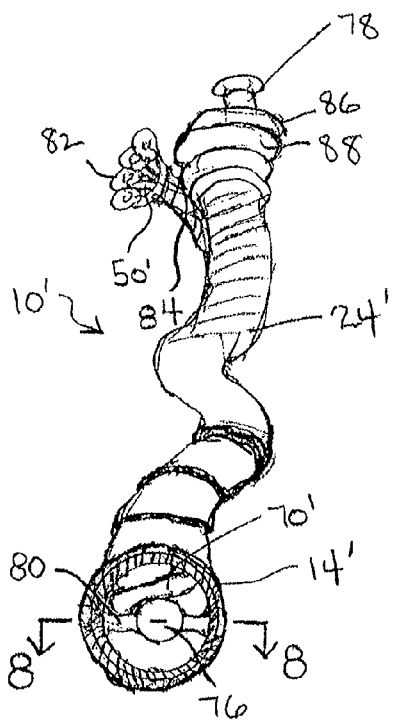
FIG. 7 is a perspective view of another embodiment of an intubation device having a base tube and three extension tubes in accordance with the present invention.
Figure 8:
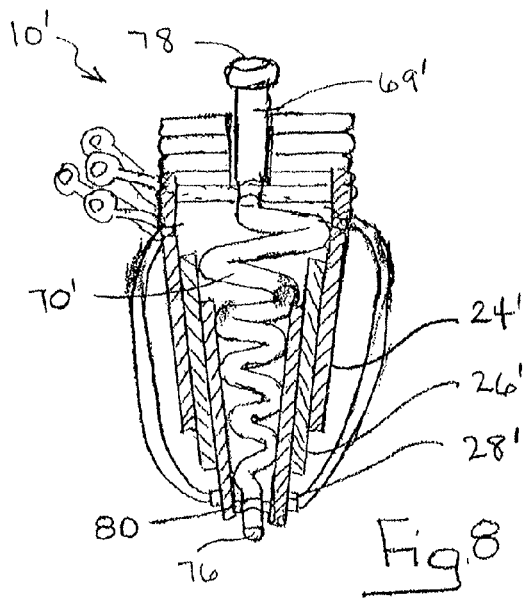
FIG. 8 is a cross sectional view of an intubation device as seen along line 8-8 in FIG. 7 but having a base tube and two extension tubes, shown in the non-extended configuration.

FIGS. 7 and 8 show another embodiment of an intubation device 10' having an optical assembly 69' to allow a user (e.g. physician) to visually monitor the advancement of the distal end 14' of the device 10' into the trachea of the patient. As shown, the optical assembly 69' can include a flexible optical fiber 70' that is coiled within the lumens of the tubes 24', 26', 28' and can straighten when the tubes 26', 28' are extended from the base tube 24'. As shown, the optical assembly also includes a distal lens 76 and a fiber-optic view finder 78 at the proximal end. Also shown, the distal end of the optical fiber 70' can be affixed to the distal end of the distal most extension tube (i.e. tube 28') using a mounting bracket 80.

FIG. 8 also shows that the tubes 24', 26', 28' may be tapered, with each tube 24', 26', 28' having a conical shape with a relatively smaller distal diameter and a relatively larger proximal diameter. FIG. 7 further shows that the proximal end of each control wire 50' can include an end cap ferrule 82 and can be placed inside a control unit 84 as shown. Typically, the extension tubes 26', 28' are straight when in a relaxed state. As a consequence, the ferrule 82 on each wire 50' is biased toward the control unit 84 and is pulled from the control unit 84 to selectively retract or bend an extension tube 26', 28'. For the embodiment shown in FIG. 7, the base tube 24' is rigid and pre-bent into a desired configuration, and can be formed with a handle 86 having one or more grips 88 to facilitate insertion into the upper respiratory tract of the patient.

Figure 9:
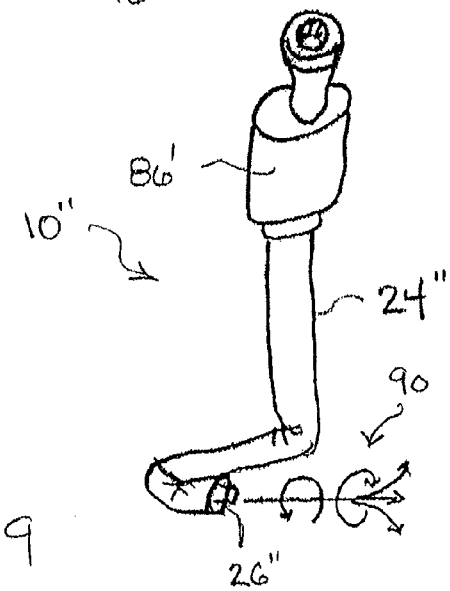
FIG. 9 is a perspective view of another embodiment of an intubation device having a pre-bent base tube and with the extension tubes in a non-extended configuration.
Figure 10:
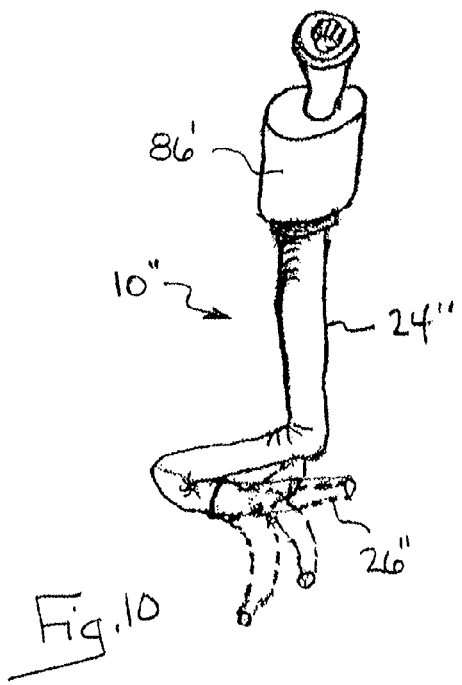
FIG. 10 is a perspective view of intubation device shown in FIG. 9 illustrating various positions of the extension tubes.

FIG. 9 shows another embodiment of an intubation device 10" having rigid, pre-bent base tube 24" and handle 86'. FIG. 9 also shows that the device 10" can include an extension tube 26" and indicates, via arrows 90 the movements of the extension tube 26" that are possible including extension, rotation and bending movements. FIG. 10 illustrates different shapes of the extension tube 26" that are possible.

The operation of the device 10 can best be appreciated with reference to FIG. 1. First, the device 10 is sterilized and assembled as described above. Next, the distal end 14 of the device 10 is inserted into a patient's nose or mouth and advanced through the upper respiratory tract. In some cases, this advancement can be with the assistance of a conventional laryngoscope (not shown). In other cases, the device is made with a rigid proximal portion (i.e. basetube 24) to anatomically fill the upper airway. Once in the upper respiratory tract, the optical assembly 69 can be used to visually monitor the advancement of the distal end 14 and identify certain anatomical features to ensure that the device 10 is steered into the trachea 16 rather than the esophagus 92. These anatomical features can include the vocal chords and/or tracheal rings. Once the correct path is identified, one or more of the control wires 50a,b can be manipulated to bend the distal end 14 of the device 10 and steer the intubation device 10 into a patient's trachea 16. The device can then be secured to the patient 12 using customary techniques.

Figure 11:
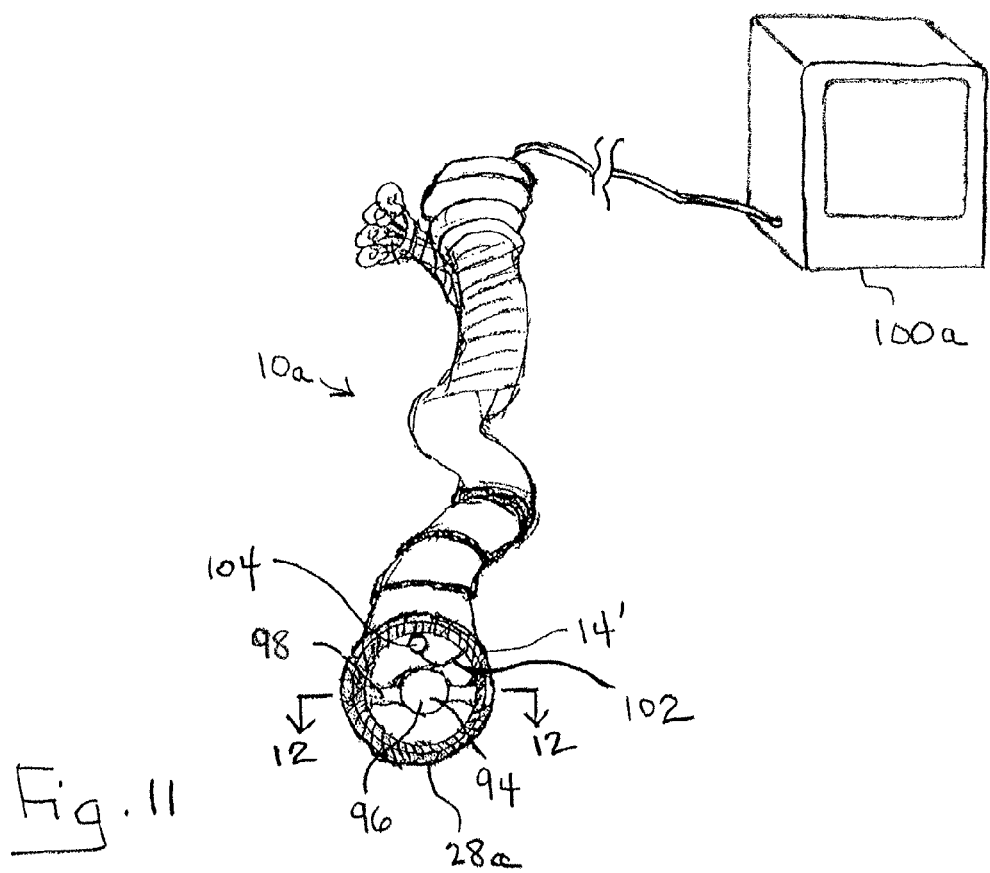
FIG. 11 is a perspective view of another embodiment of an intubation device having a camera system in accordance with the present invention.

FIG. 11 shows another embodiment of an intubation device 10a having a camera system 94 in accordance with the present invention to allow a user (e.g. physician) to visually monitor the advancement of the distal end 14' of the tube assembly into the trachea of a patient. For this embodiment, the camera system 94 can include a sensor portion 96, a monitor portion 100a and one or more conductive wire(s) 102. For the camera system 94, the sensor portion 96 can be attached to the distal end of the most distal extension tube 28a using bracket 98. For example, the sensor portion 96 can be an electronic, digital image sensor such as a CMOS sensor or a charge coupled device (CCD). The sensor portion 96 can be used to capture video and/or still images which can be transferred, via wire 102 to the monitor portion 100a. In some cases, the output from the sensor portion 96 can be stored, for example in computer memory (not shown) for subsequent playback or processing. The monitor portion 100a of the camera system can be provided as a stand-alone display (FIG. 11) or an eyepiece (monitor portion 100b shown in FIG. 12. FIG. 11 also shows that an optional light source 104 can be provided at the distal end of the distal most tube 28a to illuminate the anatomical portions of the body near the distal end of the tube assembly.

Figure 12:
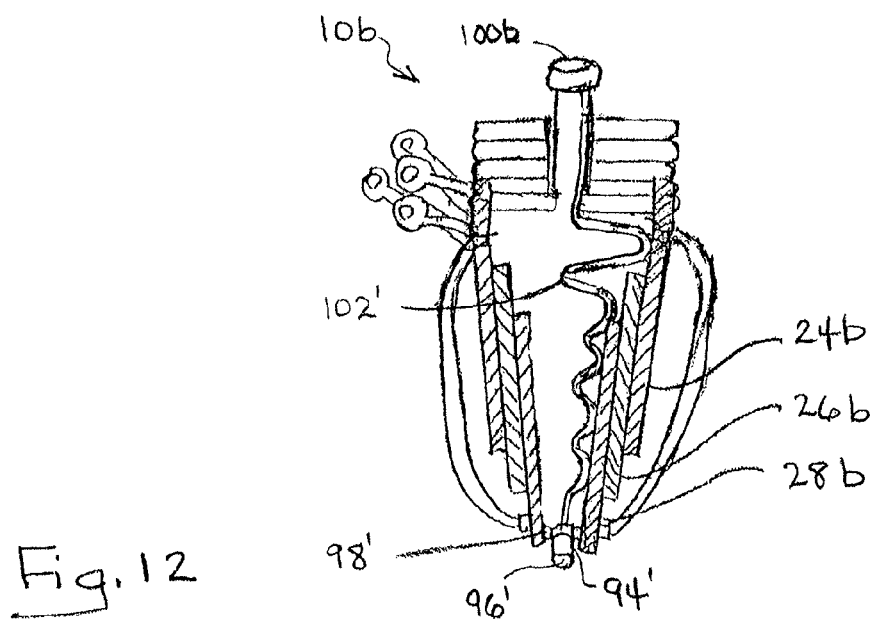
FIG. 12 is a cross sectional view of an intubation device with a camera system as seen along line 12-12 in FIG. 11 but having a base tube and two extension tubes, shown in the non-extended configuration and having a display monitor.

FIG. 12 shows another embodiment of an intubation device 10b having a camera system 94' in accordance with the present invention to allow a user (e.g. physician) to visually monitor the advancement of the distal end of the tube assembly into the trachea of a patient. For this embodiment, the camera system 94' can include a sensor portion 96', a monitor portion 100b and one or more conductive wire(s) 102'. For the camera system 94, the sensor portion 96' can be attached to the distal end of the most distal extension tube 28b using bracket 98'. As shown, the monitor portion 100b of the camera system can be provided as an eyepiece. The conductive wire 102' is operably connected to the sensor portion 96' and extends through the tube assembly to the monitor portion 100b. As shown, the conductive wire 102' can include slack within the lumens of the tubes 24b, 26b, 28b and can straighten when the tubes 26b, 28b are extended from the base tube 24b. The camera systems 94, 94' shown in FIGS. 11 and 12 can be combined and used with the optical fiber shown in FIGS. 1-8 and described above.

While the particular telescopic intubation tube with distal camera and corresponding methods of use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A telescopic intubator which comprises:
    (a) a tube assembly comprising
        (i) a base tube having a proximal end and a distal end and formed with a lumen extending between the proximal end and the distal end thereof,
        (ii) a first extension tube having a proximal end and a distal end, and formed with a lumen extending between the proximal end and the distal end thereof, and mounted in the lumen of the base tube for a fore-and-aft movement therewith, the proximal end of the first extension tube being distal to the proximal end of the base tube; wherein the tube assembly decreases in diameter; and
        (iii) a second extension tube, wherein the second extension tube has a proximal end and a distal end and is mounted in the lumen of the first extension tube for a fore-and-aft movement therein to selectively extend the distal end of the second extension tube beyond the distal end of the first extension tube, wherein there is no relative rotation between adjacent tubes in the tube assembly;
    (b) a first set of control wires having distal ends attached to the distal end of the first extension tube for bending the first extension tube and reciprocally moving the first extension tube fore-and-aft relative to the base tube, and a second set of control wires having distal ends attached to the second extension tube for bending the second extension tube and reciprocally moving the second extension tube fore-and-aft relative to the first extension tube and base tube to advance the first and/or second extension tube into a trachea of a patient; and
    (c) an optical assembly comprising an eyepiece mounted on the proximal end of the base tube and an optical fiber extending from the eyepiece to the distal end of the second extension tube for visually monitoring an advancement of the intubator into a trachea of a patient.

2. The telescopic intubator of claim 1, further comprising a light source attached to the distal end of the second extension tube.

3. The telescopic intubator of claim 1, wherein the first set of control wires are attached to an external surface of the distal end of the first extension tube and the second set of control wires are attached to an external surface of the second extension tube tube.

4. The telescopic intubator of claim 1, wherein the first set of control wires are attached to an internal surface of the distal end of the first extension tube and the second set of control wires are attached to an internal surface of the second extension tube.

5. A telescopic intubator which comprises:
    (a) a tube assembly comprising
        (i) a base tube having a proximal end and a distal end and formed with a lumen extending between the proximal end and the distal end thereof;
        (ii) a first extension tube having a proximal end and a distal end, and formed with a lumen extending between the proximal end and the distal end thereof, and mounted in the lumen of the base tube for a fore-and-aft movement therewith, the proximal end of the first extension tube being distal to the proximal end of the base tube; wherein the tube assembly decreases in diameter; and
        (iii) a second extension tube, wherein the second extension tube has a proximal end and a distal end and is mounted in the lumen of the first extension tube for a fore-and-aft movement therein to selectively extend the distal end of the second extension tube beyond the distal end of the first extension tube, wherein there is no relative rotation between adjacent tubes in the tube assembly;
    (b) a first set of control wires having distal ends attached to the distal end of the first extension tube for bending the first extension tube and reciprocally moving the first extension tube fore-and-aft relative to the base tube, and a second set of control wires having distal ends attached to the second extension-tube for bending the second extension tube and reciprocally moving the second extension tube fore-and-aft relative to the first extension tube and base tube to advance the first and/or second extension tube into the trachea of a patient; and
    (c) an optical assembly comprising a camera system having a sensor portion mounted in the distal end of the second extension tube for visually monitoring an advancement of the intubator into a trachea of a patient.

6. The telescopic intubator of claim 5, wherein the camera system comprises a monitor portion and at least one conductive wire connecting the sensor portion to the monitor portion.

7. The telescopic intubator of claim 6, wherein the monitor portion is a stand-alone display monitor.

8. The telescopic intubator of claim 5, wherein the first set of control wires are attached to an external surface of the distal end of the first extension tube and the second set of control wires are attached to an external surface of the second extension tube.

9. The telescopic intubator of claim 5, wherein the first set of control wires are attached to an internal surface of the distal end of the first extension tube and the second set of control wires are attached to an internal surface of the second extension tube.

10. A method for intubating a patient, the method comprising the steps of:
   inserting the distal end of the second extension tube of the telescopic intubator of claim 1 into a natural opening of the patient;
   reciprocally moving the second extension tube fore-and-aft relative to the first extension tube;
   selectively bending the second extension tube to advance at least one distal end of the telescopic intubator into a trachea of the patient; and
   visually monitoring an advancement of the distal end of the second extension tube into the trachea of the patient.

11. A method for intubating a patient, the method comprising the steps of:
   inserting the distal end of the second extension of the telescopic intubator of claim 5 into a natural opening of the patient;
   reciprocally moving the second extension tube fore-and-aft relative to the first extension tube;
   selectively bending the second extension tube to advance at least one distal end of the telescopic intubator into a trachea of the patient; and
   visually monitoring an advancement of the distal end of the second extension tube into the trachea of the patient.

* * * * *